United States Patent
Wieters et al.

(10) Patent No.: US 9,955,855 B2
(45) Date of Patent: May 1, 2018

(54) ELECTRICAL CONNECTION PIECE FOR A VIDEO ENDOSCOPE, VIDEO ENDOSCOPE, AND METHOD FOR PRODUCING AN ELECTRICAL CONNECTION IN A VIDEO ENDOSCOPE

(71) Applicant: OLYMPUS WINTER & IBE GMBH, Hamburg (DE)

(72) Inventors: Martin Wieters, Hamburg (DE); Sebastian Jungbauer, Hamburg (DE); Alrun Thuemen, Hamburg (DE); Nils Torkuhl, Gross Vollstedt (DE); Enno Ehlers, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 763 days.

(21) Appl. No.: 14/457,501

(22) Filed: Aug. 12, 2014

(65) Prior Publication Data

US 2014/0371530 A1    Dec. 18, 2014

Related U.S. Application Data

(63) Continuation of application No. PCT/EP2013/000347, filed on Feb. 5, 2013.

(30) Foreign Application Priority Data

Feb. 13, 2012   (DE) .................. 10 2012 202 133

(51) Int. Cl.
*A61B 1/06*    (2006.01)
*A61B 1/00*    (2006.01)
(Continued)

(52) U.S. Cl.
CPC ........ *A61B 1/00124* (2013.01); *A61B 1/0011* (2013.01); *A61B 1/00114* (2013.01);
(Continued)

(58) Field of Classification Search
CPC ............ A61B 1/00101; A61B 1/00105; A61B 1/0011; A61B 1/00112; A61B 1/00114;
(Continued)

(56) References Cited

U.S. PATENT DOCUMENTS 6,030,339 A * 2/2000 Tatsuno ............. A61B 1/00195
                                                    600/112
6,080,101 A * 6/2000 Tatsuno ............. A61B 1/00124
                                                    348/65
(Continued)

FOREIGN PATENT DOCUMENTS

CN       102325489 A     1/2012
DE   102006015176 B3     7/2007
(Continued)

OTHER PUBLICATIONS

International Search Report dated May 15, 2013 issued in PCT/EP2013/000347.
(Continued)

*Primary Examiner* — Anhtuan T Nguyen
*Assistant Examiner* — William Chou
(74) *Attorney, Agent, or Firm* — Scully, Scott, Murphy & Presser, P.C.

(57) ABSTRACT

The invention relates to an electrical connection piece for a video endoscope having a hermetically closed video unit in a shaft of the endoscope, a video endoscope, and a method for producing an electrical connection in a video endoscope. The electrical connection piece according to the invention includes an at least partially flexible printed circuit board having conductive tracks, wherein the printed circuit board has a base surface with openings for contact pins of a hermetic feedthrough, and a flexible first arm and a flexible second arm that branch off in different, in particular opposite, directions from the base surface, wherein the first arm (Continued)

and the second arm each have a flat end surface at the respective ends facing away from the base surface, wherein the conductive tracks extend between the openings on the base surface and electrical contacting surfaces in the end surfaces.

14 Claims, 2 Drawing Sheets

(51) Int. Cl.
*A61B 1/04* (2006.01)
*G02B 23/24* (2006.01)
*A61B 1/05* (2006.01)
*H01R 12/77* (2011.01)
*H01R 13/6461* (2011.01)
*H05K 1/11* (2006.01)
*H05K 3/34* (2006.01)

(52) U.S. Cl.
CPC ............ *A61B 1/05* (2013.01); *G02B 23/2476* (2013.01); *H01R 12/771* (2013.01); *H01R 12/772* (2013.01); *H01R 13/6461* (2013.01); *H05K 1/118* (2013.01); *H05K 3/341* (2013.01); *A61B 1/00105* (2013.01); *Y10T 29/49149* (2015.01)

(58) Field of Classification Search
CPC . A61B 1/00121; A61B 1/00124; A61B 1/042; A61B 1/05; A61B 1/051; A61B 1/053; G02B 23/2484

USPC ....... 600/109, 110, 112, 129, 132, 160, 174, 600/175; 439/67, 77, 492, 493, 499
See application file for complete search history.

(56) References Cited

U.S. PATENT DOCUMENTS

| | | |
|---|---|---|
| 2004/0167378 A1 | 8/2004 | Ando |
| 2004/0263616 A1 | 12/2004 | Yamaguchi |
| 2005/0228226 A1 | 10/2005 | Muckner |
| 2007/0038024 A1* | 2/2007 | Nakamura ......... A61B 1/00114 600/110 |
| 2008/0249363 A1* | 10/2008 | Nakamura ........... A61B 1/0011 600/132 |
| 2009/0082624 A1 | 3/2009 | Joko et al. |
| 2012/0029287 A1 | 2/2012 | Wieters et al. |

FOREIGN PATENT DOCUMENTS

| | | |
|---|---|---|
| DE | 102009011479 A1 | 9/2010 |
| JP | H10-028672 A | 2/1998 |
| JP | 2000-333903 A | 12/2000 |
| JP | 2005-020313 A | 1/2001 |
| JP | 2006-255320 A | 9/2006 |

OTHER PUBLICATIONS

Chinese Office Action dated Dec. 2, 2015 together with a Search Report from related Chinese Patent Application No. 201380006688.8.

* cited by examiner

ELECTRICAL CONNECTION PIECE FOR A VIDEO ENDOSCOPE, VIDEO ENDOSCOPE, AND METHOD FOR PRODUCING AN ELECTRICAL CONNECTION IN A VIDEO ENDOSCOPE

CROSS-REFERENCE TO RELATED APPLICATION

The present application is a continuation of PCT/EP2013/000347 filed on Feb. 5, 2013, which is based upon and claims the benefit to DE 10 2012 202 133.7 filed on Feb. 13, 2012, the entire contents of each of which are incorporated herein by reference.

BACKGROUND

Field

The invention relates to an electrical connection piece for a video endoscope having a hermetically closed video unit in a shaft of the video endoscope, a video endoscope, a use and a method for producing an electrical connection in a video endoscope.

Prior Art

With video endoscopes, there are typically optics at the distal tip of the endoscope shaft, for example a straight-ahead viewing or sideways viewing objective lens followed by one image sensor or a pair of image sensors that convert the received light into electronic image information, and conduct this information as electronic signals toward the proximal end. Pairs of image sensors can be used, for example with stereo video endoscopes, for producing a spatial impression, for improving the color rendering, or for setting different sensitivities or different analyses, for which different optical properties are necessary.

The electrical lines with which the electrical signals are further transmitted in the interior of the endoscope shaft, can be cables with multiple shielded and unshielded wires, flexible printed circuit boards or similar.

With video endoscopes of the applicant of the present invention, both the optics and also the image sensor are located in a hermetically sealed chamber. Therefore, there must be a hermetically sealed passage to these electrical lines. With corresponding video endoscopes, the hermetically sealed feedthrough is accomplished using metal pins, or respectively metal contact pins, molded in glass. The electrical lines are soldered directly to the metal pins.

Video endoscopes with a lateral viewing direction require a mechanical image rotation for the functioning thereof. With the image rotation, the electrical lines become twisted between the image sensor or image sensors and the hermetic passage. The cable is soldered to the pins of the hermetic passage so that the central axis thereof is located on the rotational plane of the rotation. Because the cable is spliced out and the individual wires are soldered to the hermetic connector, the cable can become consistently twisted with little force.

The soldering of the individual wires to the individual contact pins is however laborious, prone to mix-ups, associated with a high process risk, and thus costly in the production.

SUMMARY

In contrast, an object of the present invention is to make possible an appropriate contact in a video endoscope, in particular having a rotatable lateral viewing direction, that is easy to produce and permits twisting with low force within the hermetically sealed chamber in the video endoscope.

This object is solved by an electrical connection piece for a video endoscope having a hermetically closed video unit in a shaft of the video endoscope, comprising an at least partially flexible printed circuit board having conductive tracks, wherein the printed circuit board has a base surface including openings for contact pins of a hermetic passage and a flexible first arm and a flexible second arm that branch off in different, in particular opposite, directions from the base surface, wherein the first arm and the second arm each have a flat end surface at their respective ends facing away from the base surface, wherein the conductive tracks extend between the openings on the base surface and electrical contacting surfaces in the end surfaces.

The electrical connection piece according to the invention solves the problem of the elaborate contact to the hermetic feedthrough in that an adapter printed circuit board is realized by means of the at least partially flexible printed circuit board, which can be soldered easily to the hermetic feedthrough. The wires of the cable are accordingly soldered to the contacting surfaces on the end surfaces of the printed circuit board. The advantage here is that the arrangement of the solder pads on the printed circuit board is planar so that the soldering becomes very easy and therefore inexpensive.

During soldering of the base surface to the contact pins of the hermetic passage, both arms are not yet placed on each other so that the base surface, or the solder pads, are exposed and can be reached easily. The soldering here can be easily automated. Even in the event of manual soldering, an unintended exchange of the contacts at this location is excluded.

Preferably the base surface and/or the end surfaces(s) of the flexible printed circuit board is or are stiffened and/or less flexible than the arms. If the base surface is stiffened and/or less flexible than the arms, the base surface of the printed circuit board can be slid easily onto the contact pins of the hermetic feedthrough, and can be fixed to the respective location in a simple manner. This also facilitates the subsequent soldering. If the end surfaces are stiffened or less flexible than the arms, this facilitates the connection to a further electrical connection element.

The stiffening stabilizes the connection piece and prevents an undesirable loosening of electrical connections on the path from the image sensor to the handle of the video endoscope.

The function of the rotation of the image sensor in the video endoscope is facilitated when the first arm and the second arm preferably have the same length and can be placed or are placed flat on top of each other, wherein the end surfaces in the stacked state point away from the base surface and in the stacked state form a substantially symmetrical triangle together with the base surface, wherein the end surfaces placed on top of each other lie substantially on a central axis, or respectively the axis of rotation of the video unit. As a result of this, the image rotation is further guaranteed because the electrical connection lies on or respectively in the vicinity of, the axis of rotation. In order to attain this, the printed circuit board is implemented so that it is bent on each of two sides so that the ends meet in the vicinity of the axis of rotation. Thus, twisting of the further connection elements is not preferred in any direction and therefore the wear is minimized. The end surfaces lie on top of each other and are possibly arranged symmetrically with respect to the central axis, or respectively the axis of rotation.

The printed circuit board, in the state of the arms lying on top of each other, preferably has a continuous ground plane on each of the inner lying sides. Thus, the ground plane lies between the conductive tracks on the arms, and shields these against each other, whereby signal disruptions due to crosstalk are effectively prevented. The ground planes can be have a common potential or be at a separate potential.

Further preferably, there is a, in particular flat, stabilizing body, which is arranged between the end surfaces lying on top of each other, wherein the stabilizing body in particular comprises a material by means of which signal crosstalk in the conductive tracks of the end surfaces of the first arm and the second arm is prevented or reduced. The stabilizing body ensures a further improvement of the fastening of the end surfaces to each other so that the continuous contact is more stable and less susceptible to damage. At the same time, the stabilizing body separates the end surfaces further from each other, and thus also the signal lines on the end surfaces, so that a capacitive coupling of conductive tracks is minimized among each other and signal crosstalk is effectively prevented.

The implementation of the printed circuit board according to the invention, having two end surfaces, which are placed back-to-back on each other, allows a high number of conductors to be connected so that also a plurality of image sensors can be connected, for example two image sensors.

As a contact, soldering to the contacting surfaces of the end surfaces of the printed circuit board can be provided, or for example a plug connection which can be accomplished using a possibly pre-produced cable connection having plug contacts to the image sensor.

Preferably there is a connection element that penetrates the end surfaces and connects them together, in particular formed as a two-sided mushroom shaped projection formed on the stabilizing body. Thus a retaining function is implemented for the end surfaces and for the electrical connection piece. The connection element can be a screw or a rivet. Alternatively, the end surfaces can also be bonded together or to the stabilizing body.

Preferably the base surface of the printed circuit board is plugged with the openings thereof over contact pins of a hermetic feedthrough and soldered to the contact pins. Here, the base surface preferably does not lie flat on a surface of the hermetic feedthrough, in order to prevent solder from penetrating into the intermediate gap due to a capillary effect, causing short circuits.

The contacting surfaces are preferably connected to the end surfaces with contacts of a further electrical connection element, in particular one or more cables or one or more flexible printed circuit boards, wherein the contacts are established particularly using soldering or by means of a plug connection.

The electrical connection piece according to the invention is simple to produce and ensures low costs and high process stability with the production.

The object addressed by the invention is also solved by a video endoscope having a hermetically closed video unit in a shaft of the endoscope, having an electrical connection piece according to the invention as described above.

In addition, an object of the invention is solved by a use of a previously described electrical connection piece according to the invention in a video endoscope having a hermetically sealed video unit in a shaft of the endoscope.

Finally, an object of the invention is also solved by a method for producing an electrical connection in a video endoscope having a hermetically closed video unit in a shaft of the endoscope, that is further developed in that a base surface of an at least partially flexible printed circuit board having openings, is plugged onto contact pins of a hermetic feedthrough of the video unit, the contact pins are soldered to contacting surfaces of conductive tracks at the openings of the printed circuit board, a first arm and a second arm are bent towards each other, and end surfaces of the arms are placed on top of each other and are connected together, wherein contacting surfaces of the conductive tracks are arranged on the end surfaces on the sides of the end surfaces facing away from each other, wherein then electrically conducting connections of the end surfaces to electrical conductors of a further electrical connection element are established. The end surfaces are preferably placed on top of each other so that they both point away from the base surface.

An electrical connection according to the invention is produced by means of this method. The further named components for the connection piece according to the invention are appropriately integrated in further method steps according to the invention.

The features, properties, and advantages named for the individual invention objects, thus the electrical connection piece, the use and the method for producing an electrical connection in a video endoscope, also apply without restriction to the respective other invention objects, which relate to each other.

Further characteristics of the invention will become apparent from the description of the embodiments according to the invention together with the claims and the included drawings. Embodiments according to the invention can fulfill individual characteristics or a combination of several characteristics.

BRIEF DESCRIPTION OF THE DRAWINGS

The invention is described below, without restricting the general intent of the invention, based on exemplary embodiments in reference to the drawings, whereby we expressly refer to the drawings with regard to the disclosure of all details according to the invention that are not explained in greater detail in the text. The figures show.

DETAILED DESCRIPTION

Figure 1:
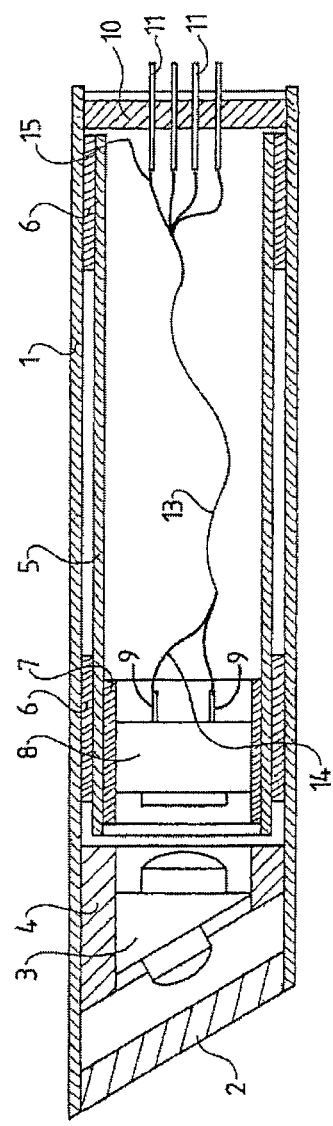
FIG. 1 is a schematic representation of a section through a known video endoscope.

In the drawings, the same or similar types of elements and/or parts are provided with the same reference numbers so that a corresponding re-introduction can be omitted.

FIG. 1 shows a schematic cross-sectional representation through a central axis of a video endoscope, as marketed by the applicant for example. The representation is of an endoscope shaft of a sideways viewing video endoscope, wherein the endoscope shaft comprises a tube 1 that hermetically encloses the elements of the video endoscope that are essential for viewing. The shaft is closed at the distal end with an oblique window 2, behind which is an object lens 3, shown here schematically, that is fastened in the tube 1 by means of an object tube 4. The object lens 3 is designed viewing obliquely. The proximal end of the tube 1 is closed by an insulating plate, or respectively a hermetic feedthrough 10, which is formed for example as a glass mold, and is penetrated by contact pins 11.

An inner tube 5 with rings 6 is mounted hermetically enclosed in the tube 1, at the proximal end of the object tube 4. In its distal end region the inner tube 5 supports an image sensor 8 with electronics, which has a distal viewing sensor chip, electronic components and similar, in a CCD-tube 7 fastened there. The proximal face side of the image sensor units supports contact pins 9 that are arranged in parallel to the axis of the tube 1.

The contact pins 9 and the contact pins 11 are to be connected together. This connection is formed by means of a flat cable or cable bundle 13 that is capable of twisting. Both ends of the cable bundle 13 are spliced out into individual cables 14, 15 each of which is soldered to a contact pin 9, 11. This embodiment permits rotation of the image sensor 8 with respect to the hermetic feedthrough 10 and the oblique viewing object lens 3 by rotating the inner tube 5 for example by means of a, e.g., magnetic, rotary drive, which is not shown.

The soldering of the cables 14, 15 to the contact pins 9, 11 is laborious and susceptible to mix-ups.

Figure 2:
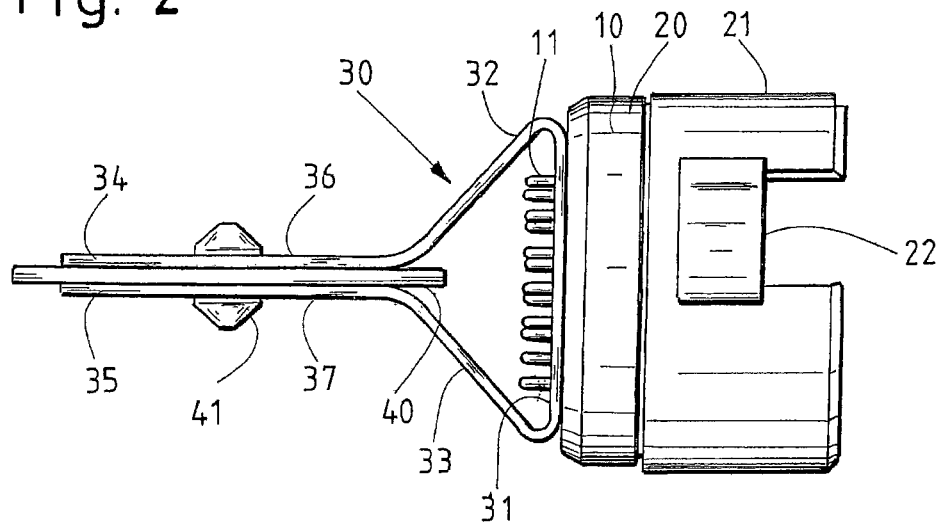
FIG. 2 is a side view of a connection piece according to the invention.

FIG. 2 shows a correspondent connection piece according to the invention, in a schematic representation from the side. On the right, the image shows the hermetic feedthrough 10 in a housing 20; joining this proximally, that is on the right in the image, there is a housing part 21 for receiving a plug connection and a screw connection location 22.

Contact pins 11 stick out from the distal side of the hermetic feedthrough 10. These pins also stick out on the proximal side, however they are perspectively covered by the housing 20. A base surface 31 of a flexible printed circuit board 30 that has openings that correspond in size and arrangement to the contact pins 11 on the hermetic passage 10, is plugged onto the distally projecting contact pins 11. Here, the base surface 31 has a separation distance to the feedthrough 10.

In FIG. 2, the base surface 31 runs above and below into a first arm 32 and a second arm 33, which are each formed flexible and support conductive tracks that are not shown individually. The flexible sections of the arms 32, 33 of the flexible printed circuit board 30 terminate in rigid end surfaces 36, 37 that lie on top of each other, wherein a stabilizing body 40 having a somewhat greater thickness is inserted in between the end surfaces 36, 37. A connection element 41 runs through the layering of the end surface 36 of the first arm 32, stabilizing body 40 and the end surface 37 of the second arm 33, and in the example embodiment according to FIG. 2 is formed as mushroom-shaped projections on both sides of the stabilizing body 40. It can also be a screw. A bonding of the flat surfaces is also possible in the scope of the invention. The backsides of the arms 32, 33 and the end surfaces 36, 37 placed on one another have ground planes which lie at a common potential, or can be placed on separate ground potentials using different contact pins 11. The ground planes can be bare or insulated electrically against each other, for instance using a coating or lacquer. The ground planes serve to shield the conductive tracks against each other in order to prevent signal crosstalk.

A triangular shape arises between the base surface 31, the first arm 32, the second arm 33 and the location at which the end surfaces 36, 37 contact each other. The contact point lies on the imaginary axis of the base surface 31, or respectively the hermetic passage 10. The end surfaces 36, 37 point away from the base surface 31.

There are contacting surfaces 34, 35, on the distal ends of the end surfaces 36 and 37, for a further contact to a further connection means, not shown.

Figure 3:
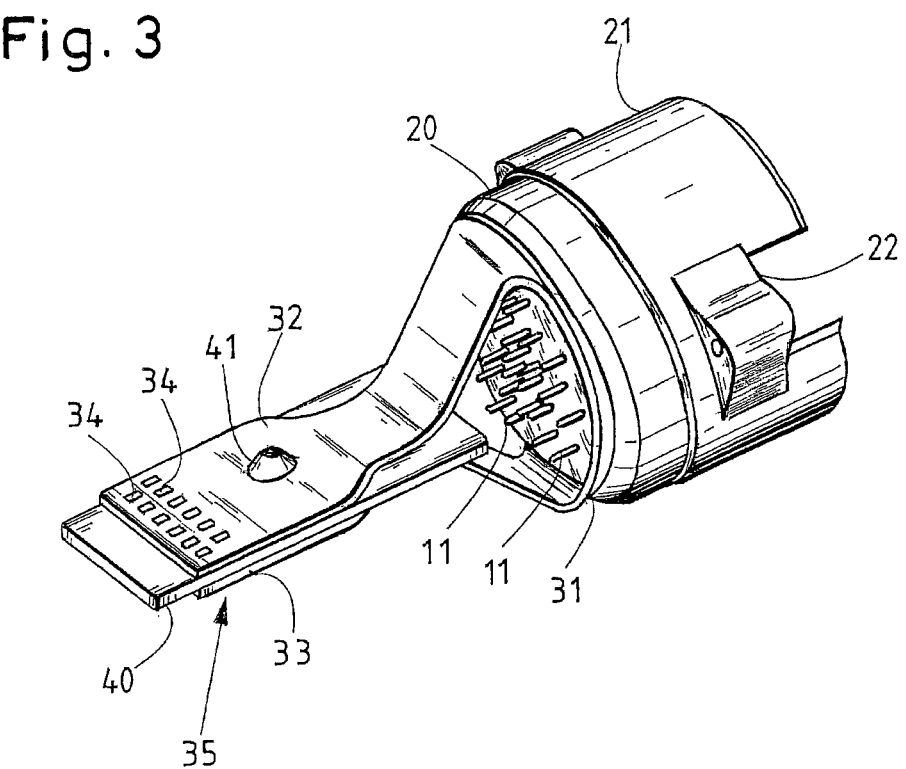
FIG. 3 is a schematic perspective representation of the electrical connection piece according to the invention according to FIG. 2.

FIG. 3 shows the connection piece from FIG. 2 in a schematic perspective representation. In addition to the details that are visible in FIG. 2, FIG. 3 also shows that a relatively great number of contacting surfaces 34, 35 can be arranged at the distal ends of the end surfaces 36, 37. The conductive tracks that originate from the contacting surfaces 34, 35 are not shown individually for reasons of clarity. A conductive track runs from each contacting surface 34 or 35 to a contact pin 11 on the base surface 31. At this location, the contact pins 11 are connected to the solder pads surrounding the openings by means of soldering, which has been applied before closing the two arms 32, 33.

The contacting surfaces 34, 35 can be soldered planar in a simple manner to flat cables, printed circuit boards or wires of a subsequent multi-conductor connecting cable that can also be spliced out. It is also possible to equip the distal end of the end surfaces 36, 37 with retaining means for a plug contact, such that a further cable having a plug can be plugged on here, thereby eliminating the need for soldering.

The electrical connection piece 2 according to FIG. 2 and FIG. 3 is a compact and stable product that is also flexible to some extent due to the flexible parts of the printed circuit board 30 and thus increases the resilience of the construction. At the same time, this permits an inexpensive and trouble-free processing. The electrical connection piece according to the invention also permits a more secure continuous contact for one or more image sensors with simultaneously rotation requiring little force, or respectively twisting of the sensor group relative to the hermetic passage.

All named characteristics, including those taken from the drawings alone, and individual characteristics, which are disclosed in combination with other characteristics, are considered individually and in combination as essential to the invention. Embodiments according to the invention can be fulfilled through individual characteristics or a combination of several characteristics.

REFERENCE LIST 1 tube
2 window
3 object lens
4 object tube
5 inner tube
6 ring
7 CCD tube
8 image sensor with electronics
9 contact pins
10 hermetic feedthrough
11 contact pins
13 cable bundle
14, 15 spliced out cable
20 housing
21 female housing part
22 screw connection location
30 flexible printed circuit board
31 base surface
32 first arm
33 second arm
34, 35 contacting surfaces
36, 37 end surfaces
40 stabilizing body
41 connection element

What is claimed is:

1. An electrical connection piece for a video endoscope having a hermetically closed video unit in a shaft of the video endoscope, the electrical connection piece comprising:
   an at least partially flexible printed circuit board having conductive tracks, the printed circuit board having a base surface with openings for contact pins of a hermetic feedthrough, a flexible first arm and a flexible second arm that branch off in different directions from the base surface;
   wherein the flexible first arm and the flexible second arm each have a flat end surface at the respective ends thereof facing away from the base surface, and the conductive tracks extend between the openings on the base surface and electrical contacting surfaces in the flat end surfaces;
   the flat end surfaces of the flexible first arm and the flexible second arm are placed flat on top of one another, wherein the flat end surfaces, in a state of lying on top of one another, point away from the base surface and form a substantially symmetrical triangle together with the base surface; and
   the flat end surfaces of the flexible first arm and the flexible second arm are substantially disposed on a central axis of rotation of the video unit.

2. The electrical connection piece according to claim 1, wherein one or more of the base surface and each of the flat end surfaces of the flexible first arm and the flexible second arm are either stiffened or less flexible than other portions of the first and second flexible arms.

3. The electrical connection piece according to claim 1, wherein the flexible first arm and the flexible second arm have the same length.

4. The electrical connection piece according to claim 1, wherein the printed circuit board includes a continuous ground plane on an inner lying side, in the state of the flat end surfaces lying on top of each other.

5. The electrical connection piece according to claim 1, further comprising a substantially flat stabilizing body arranged between the flat end surfaces.

6. The electrical connection piece according to claim 5, wherein the stabilizing body is formed of a material by means of which crosstalk of signals is reduced in the conductive tracks of the flat end surfaces of the flexible first arm and the flexible second arm.

7. The electrical connection piece according to claim 5, further comprising a connection element that penetrates and connects together the flat end surfaces.

8. The electrical connection piece according to claim 7, wherein the connection element is formed as mushroom-shaped projections on both sides of the stabilizing body.

9. The electrical connection piece according to claim 1, wherein the base surface of the printed circuit board is plugged with the openings thereof over the contact pins of a hermetic feedthrough and is soldered to the contact pins.

10. The electrical connection piece according to claim 1, wherein contacting surfaces on the flat end surfaces are connected to contacts of a further electrical connection element.

11. The electrical connection piece according to claim 10, wherein the further electrical connection element is selected from a list consisting of one or more cables and one or more flexible printed circuit boards, wherein an electrical connection is established by one of a soldering connection or a plug connection.

12. The electrical connection piece according to claim 1, wherein the flexible first arm and the flexible second arm branch off in opposite directions from the base surface.

13. A video endoscope having a hermetically closed video unit in a shaft of the video endoscope, the video endoscope comprising the electrical connection piece according to claim 1.

14. A method for producing an electrical connection in a video endoscope having a hermetically closed video unit in a shaft of an endoscope, the method comprising:
   plugging a base surface of an at least partially flexible printed circuit board with openings onto contact pins of a hermetic feedthrough of the hermetically closed video unit,
   soldering the contact pins to contacting surfaces of conductive tracks at the openings of the printed circuit board,
   bending a first arm and a second arm towards each other such that the first arm and the second arm branch off in different directions from the base surface,
   placing end surfaces of the first arm and the second arm on top of each other and connecting the end surfaces together such that the end surfaces, in a state of lying on top of one another, point away from the base surface and form a substantially symmetrical triangle together with the base surface, and the end surfaces of the first arm and the second arm are substantially disposed on a central axis of rotation of the video unit, and
   arranging contacting surfaces of the conductive tracks on the sides of the end surfaces facing away from each other such that electrically conducting
   connections of the end surfaces to electrical conductors of a further electrical connection element are established.

* * * * *